(12) United States Patent
Tai

(10) Patent No.: US 8,103,034 B2
(45) Date of Patent: Jan. 24, 2012

(54) MOUNTING DEVICE AND SPEAKER ASSEMBLY HAVING THE SAME

(75) Inventor: Chuan-Chi Tai, Taipei (TW)

(73) Assignee: Zylux Acoustic Corporation, Taipei (TW)

( * ) Notice: Subject to any disclaimer, the term of this patent is extended or adjusted under 35 U.S.C. 154(b) by 469 days.

(21) Appl. No.: 12/386,298

(22) Filed: Apr. 16, 2009

(65) Prior Publication Data

US 2010/0158298 A1    Jun. 24, 2010

(30) Foreign Application Priority Data

Dec. 23, 2008    (TW) ............................... 97223075 U

(51) Int. Cl.
*H04R 1/02* (2006.01)
*H04R 9/06* (2006.01)
(52) U.S. Cl. ......... 381/332; 381/335; 381/386; 381/387
(58) Field of Classification Search .................. None
See application file for complete search history.

(56) References Cited

U.S. PATENT DOCUMENTS

| | | | |
|---|---|---|---|
| 4,565,905 A * | 1/1986 | Nation | 381/186 |
| 6,941,646 B2 * | 9/2005 | Suhara | 29/740 |
| 7,676,045 B2 * | 3/2010 | Merrey et al. | 381/87 |
| 2007/0121988 A1 * | 5/2007 | Merrey et al. | 381/386 |
| 2010/0158298 A1 * | 6/2010 | Tai | 381/332 |

FOREIGN PATENT DOCUMENTS

TW    M338520    8/2008

OTHER PUBLICATIONS

English Abstract of Taiwan Utility Model No. M338520.

* cited by examiner

*Primary Examiner* — Marlo Fletcher
(74) *Attorney, Agent, or Firm* — Allston L. Jones; Peters Verny, LLP

(57) ABSTRACT

A mounting device includes a positioning frame mounted with an electronic device, and two clamping mechanisms. Each clamping mechanism includes a sliding member movable vertically relative to the positioning frame, a clamping member movable horizontally relative to the sliding member between an extended position and a retracted position, a spring for biasing the clamping member toward the extended position, and a height-adjusting member operable to adjust the vertical position of the sliding member relative to the positioning frame. The clamping members can be moved to the retracted positions to allow for movement of the clamping members through a mounting hole in a horizontal plate, after which the height-adjusting members is operable to move the clamping members toward the positioning frame to thereby clamp the plate between the positioning frame and the clamping members.

16 Claims, 15 Drawing Sheets

MOUNTING DEVICE AND SPEAKER ASSEMBLY HAVING THE SAME

CROSS-REFERENCE TO RELATED APPLICATION

This application claims priority of Taiwanese Application No. 097223075, filed on Dec. 23, 2008.

BACKGROUND OF THE INVENTION

1. Field of the Invention

This invention relates to a mounting device, and more particularly to a mounting device that is disposed within a mounting hole in a horizontal plate (e.g., a ceiling) for mounting an electronic device (e.g., a speaker) to the plate.

2. Description of the Related Art

Referring to FIGS. 1, 2, and 3, a conventional speaker assembly disclosed in Taiwanese Patent Number M338520 includes a speaker 11, an annular frame 12 attached to a bottom end of the speaker 11, and two clamping devices 13. Each of the clamping devices 13 includes a connecting member 14 mounted fixedly to a corresponding side surface 111 of the speaker 11, a pivotable clamping member 15, and a movable member 16. A first bolt 17 extends through a first hole 151 in the pivotable member 15, and engages a threaded hole 141 in the connecting member 14 such that the pivotable member 15 is rotatable about the first bolt 17. A second bolt 17' extends through a horizontal hole 161 in the movable member 16 and a second hole 152 in the pivotable member 15. An adjustment bolt 18 engages a vertical threaded hole 162 in the movable member 16. A clearance is formed between the second bolt 17' and the movable member 16 so that, when the movable member 16 moves vertically on the adjustment bolt 18, the pivotable member 15 can rotate about the first bolt 17.

When it is desired to mount the conventional speaker assembly to a ceiling 10, referring to FIG. 2, the pivotable members 15 are first pivoted to vertical positions to allow the speaker 11 and the pivotable members 15 to be moved through a mounting hole 101 in the ceiling 10. Next, the user rotates the adjustment bolts 18 one at a time with one hand to move the movable members 16 downwardly while supporting the annular frame 12 with the other hand. Hence, the pivotable members 15 are pivoted respectively and downwardly about the first bolts 17 until clamping portions 153 of the pivotable members 15 come into contact with a top surface of the ceiling 10, thereby clamping the ceiling 10 between the annular frame 12 and the clamping plate portions 153. As such, it is difficult to mount the conventional speaker assembly to the ceiling 10.

SUMMARY OF THE INVENTION

The object of this invention is to provide a mounting device that can mount an electronic device to a horizontal plate with ease.

According to this invention, a mounting device is used for mounting an electronic device to a horizontal plate, and includes a positioning frame mounted with the electronic device, and at least two clamping mechanisms. Each of the clamping mechanisms includes a sliding member movable vertically relative to the positioning frame, a clamping member movable horizontally relative to the sliding member between an extended position and a retracted position, a spring for biasing the clamping member toward the extended position, and a height-adjusting member operable to adjust the vertical position of the sliding member relative to the positioning frame. The clamping members can be moved to the retracted positions to allow for upward movement of the clamping members through the mounting hole, after which the height-adjusting members can be operated to move the clamping members toward the positioning frame to thereby clamp the plate between the positioning frame and the clamping members.

During assembly, the clamping members are biased to the extended positions immediately after they are moved upwardly through the mounting hole in the plate. At this time, since the distance between outer ends of the clamping members is greater than the diameter of the mounting hole, the clamping members are supported by the plate so that the height-adjusting members can be operated easily to clamp the plate between the positioning frame and the clamping members.

BRIEF DESCRIPTION OF THE DRAWINGS

These and other features and advantages of this invention will become apparent in the following detailed description of the preferred embodiments of this invention, with reference to the accompanying drawings, in which.

DETAILED DESCRIPTION OF THE FIRST PREFERRED EMBODIMENTS

Figure 1:
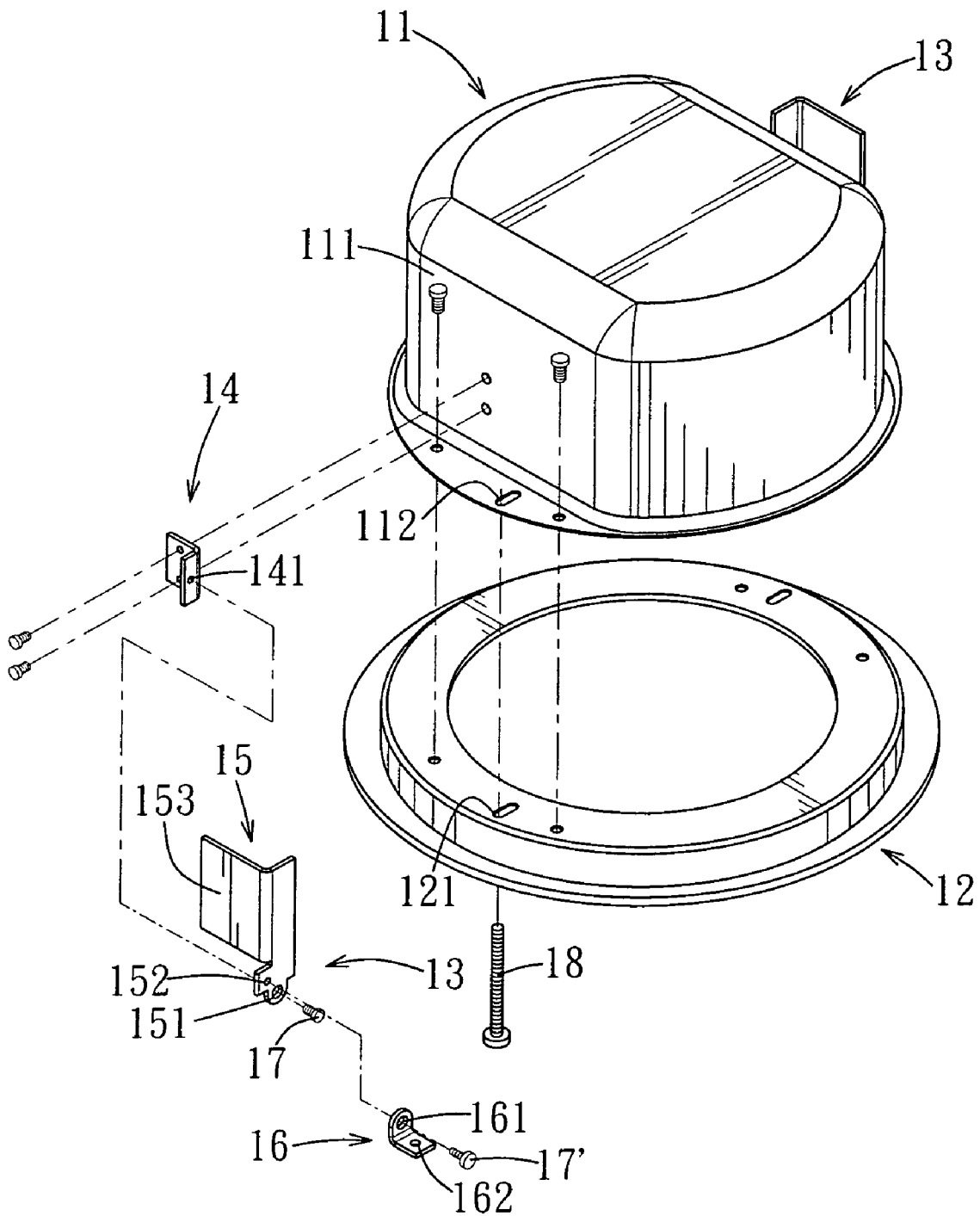
FIG. 1 is an exploded perspective view of a conventional speaker assembly disclosed in Taiwanese Patent Number M338520.
Figure 2:
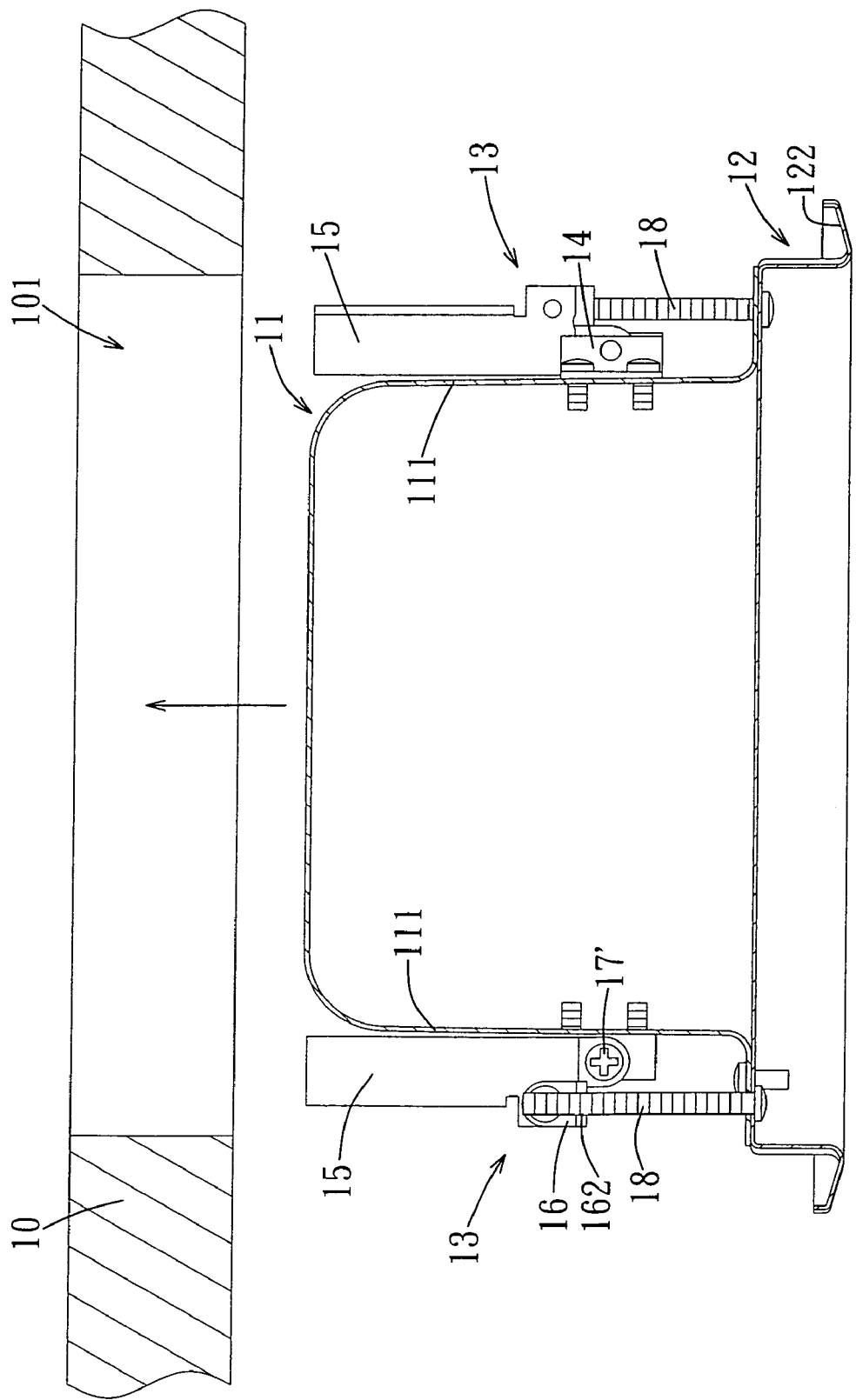
FIG. 2 is a schematic view illustrating how the conventional speaker assembly is inserted into a mounting hole in a ceiling.
Figure 3:
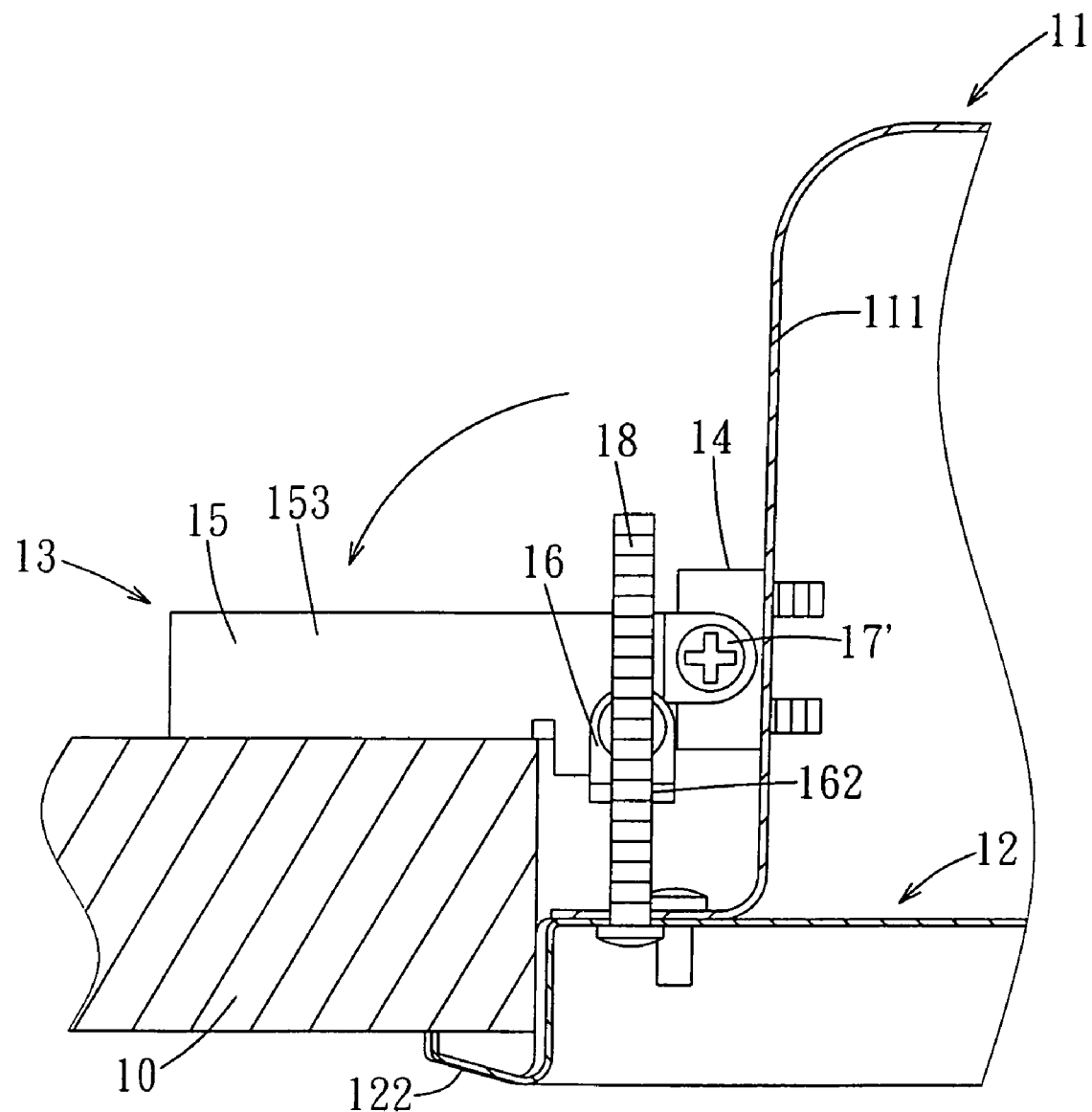
FIG. 3 is a schematic view illustrating how an adjustment bolt of the conventional speaker assembly is operated to clamp the ceiling between a pivotable member and an annular frame.
Figure 4:
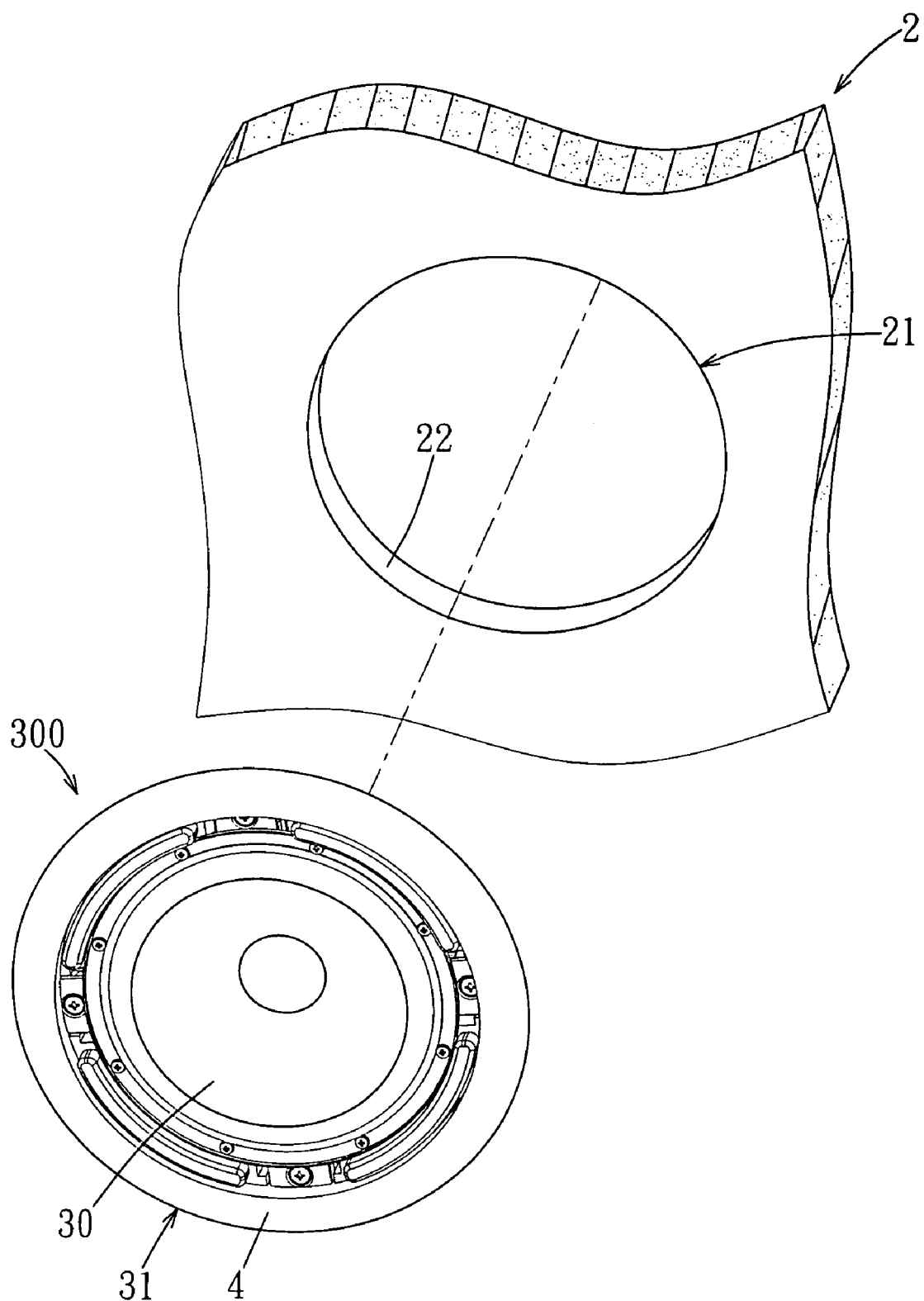
FIG. 4 is a perspective view of the first preferred embodiment of a speaker assembly according to this invention and a ceiling, the speaker assembly including a speaker and a mounting device.
Figure 5:
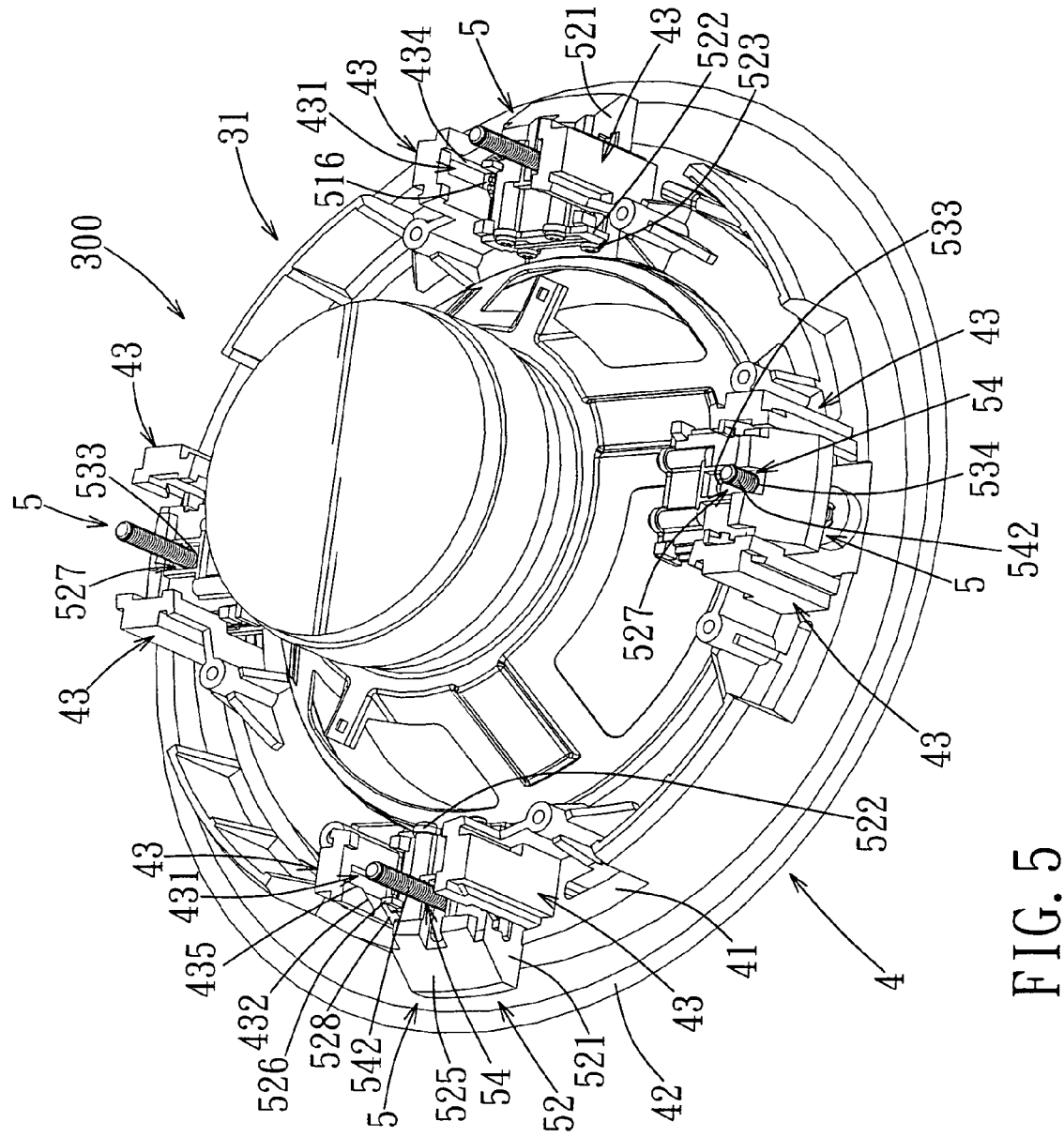
FIG. 5 is an assembled perspective view of the first preferred embodiment.
Figure 6:
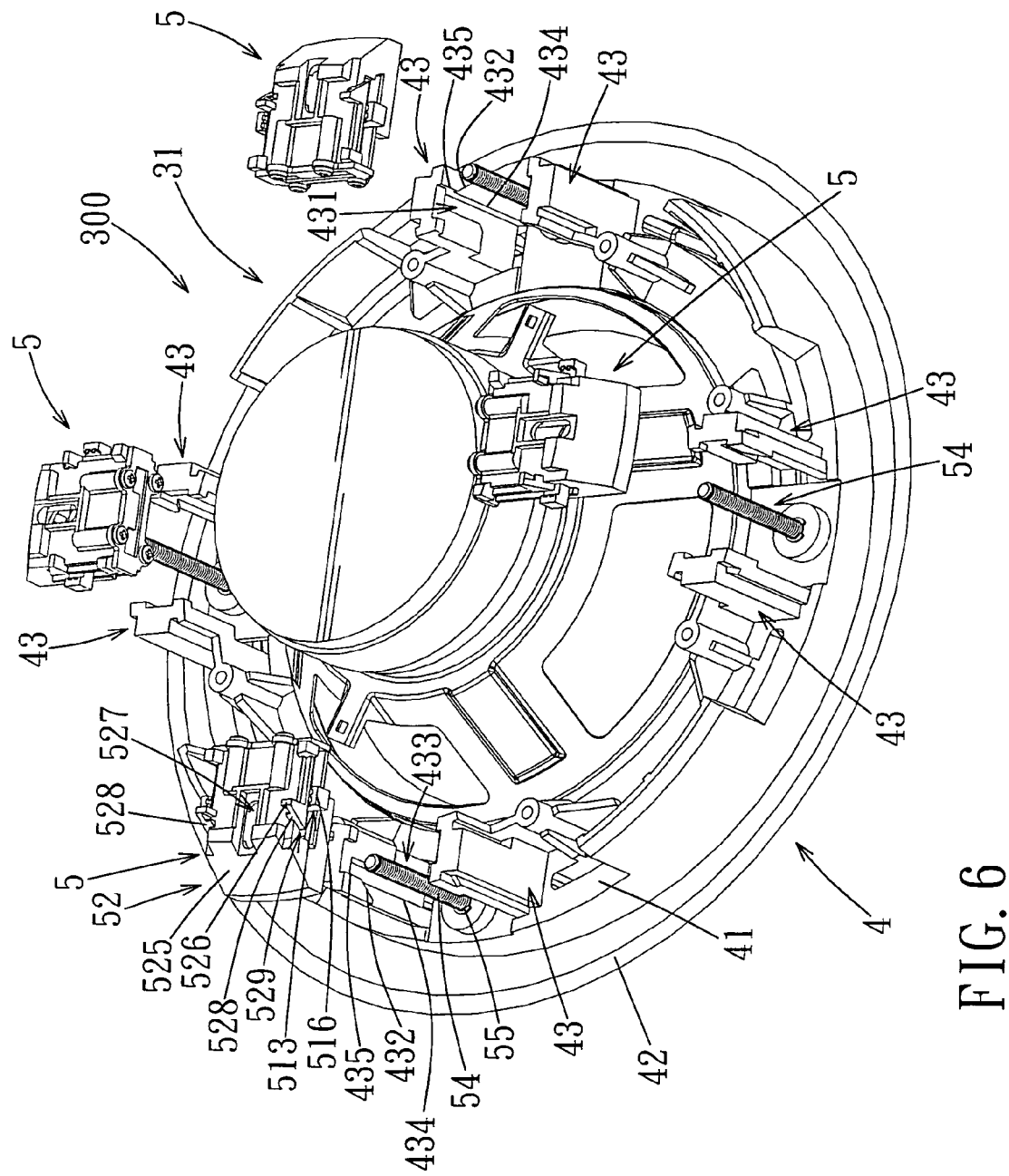
FIG. 6 is a partly exploded perspective view of the first preferred embodiment.

Referring to FIGS. 4, 5, and 6, the first preferred embodiment of a speaker assembly 300 according to this invention is mounted in a circular mounting hole 21 in a horizontal plate, such as a ceiling 2. The mounting hole 21 is defined by an inner peripheral surface 22. The speaker assembly 300 includes a speaker 30 and a mounting device 31.

Figure 7:
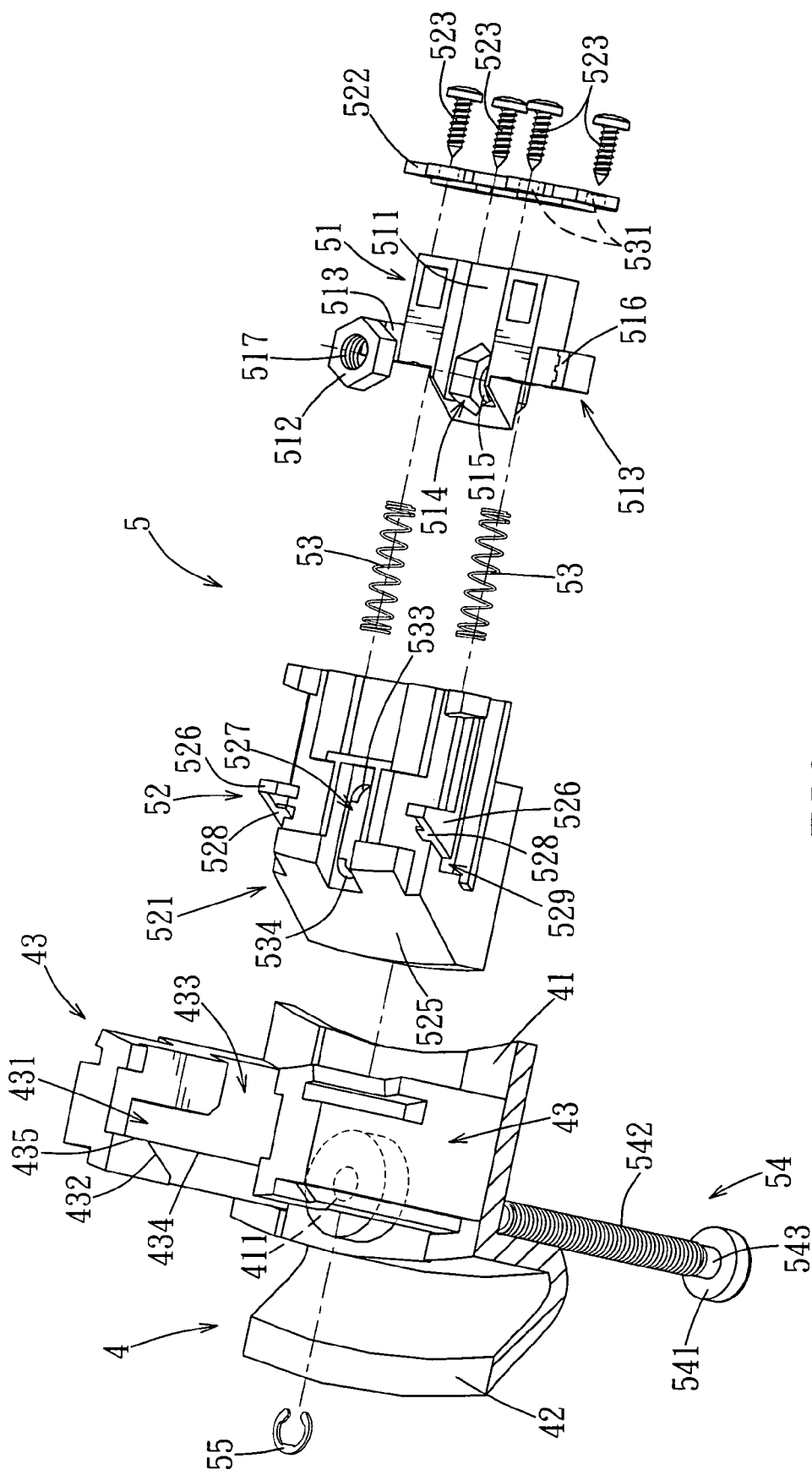
FIG. 7 is an exploded perspective view of a clamping mechanism of the first preferred embodiment.
Figure 8:
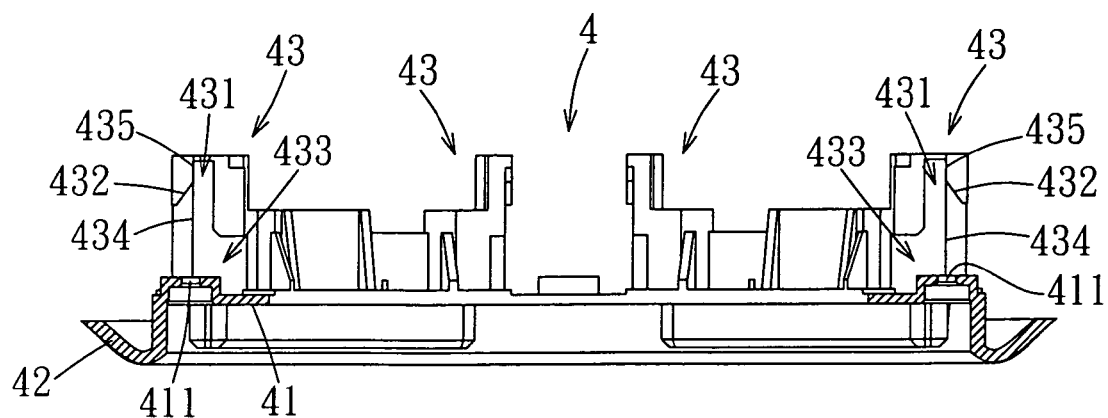
FIG. 8 is a partly sectional side view of a positioning frame of the first preferred embodiment.

With further reference to FIGS. 7 and 8, the mounting device 31 includes a positioning frame 4, and a plurality of cooperative pairs of clamping mechanisms 5 disposed on the positioning fame 4. The positioning frame 4 includes a frame body 41 disposed for mounting the speaker 30 thereon, an annular pressing ring portion 42 disposed around and extending from the frame body 41 to serve as an outer periphery of the positioning frame 4, and a plurality of protrusion units each consisting of two aligned protrusions 43. The frame body 41 has a plurality of vertical through holes 411 formed therethrough and adjacent respectively to the protrusion units. Each of the through holes 411 is located between the protrusions 43 of the corresponding protrusion unit. The protrusions 43 of each of the protrusion units extend upwardly from the frame body 41, and have two parallel vertical guide slots 431, and two aligned guiding faces 432 (i.e., each protrusion 43 has a guide slot 431 and a guiding face 432) extending upwardly and inwardly and located between the pressing ring portion 42 and the guide slots 432 in a radial direction of the positioning frame 4.

Figure 9:
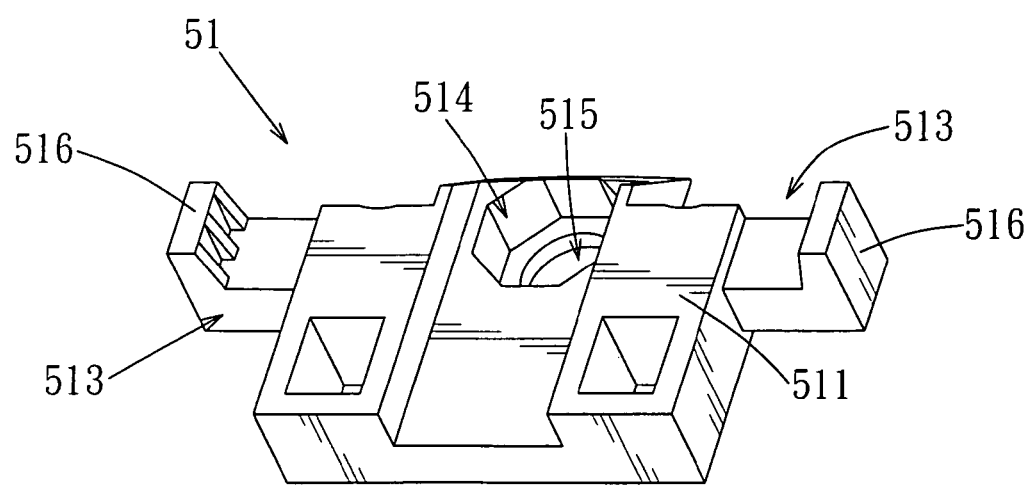
FIG. 9 is a perspective view of a sliding member of the first preferred embodiment.

Each cooperative pair of the clamping mechanisms 5 are disposed respectively at two diametrically opposite locations on the frame body 41 of the positioning frame 4. Each of the clamping mechanisms 5 is disposed between the protrusions 43 of the corresponding protrusion unit, and includes a sliding member 51, a clamping member 52, two springs 53, a vertical height-adjusting member 54, and a C-shaped retaining ring 55. With further reference to FIG. 9, each of the sliding members 51 includes a sliding body 511, a nut 512, and two extension arms 513 extending respectively from two opposite sides of the sliding body 511. Each of the sliding bodies 511 has a nut-receiving recess 514 having a hexagonal cross-section for receiving the nut 512 fittingly therein, and a central hole 515 in spatial communication with the nut-receiving recess 514. The extension arms 513 of each of the sliding members 51 have sliding ends 516 movable respectively within the vertical guide slots 431 in the protrusions 43 of the corresponding protrusion unit. As such, the sliding members 51 are movable vertically relative to the positioning frame 4. Each of the nuts 512 has a threaded hole 517 aligned with the central hole 515. Alternatively, the nuts 512 are omitted respectively from the sliding members 51, and the threaded holes 517 are formed respectively through the sliding bodies 511.

Figure 10:
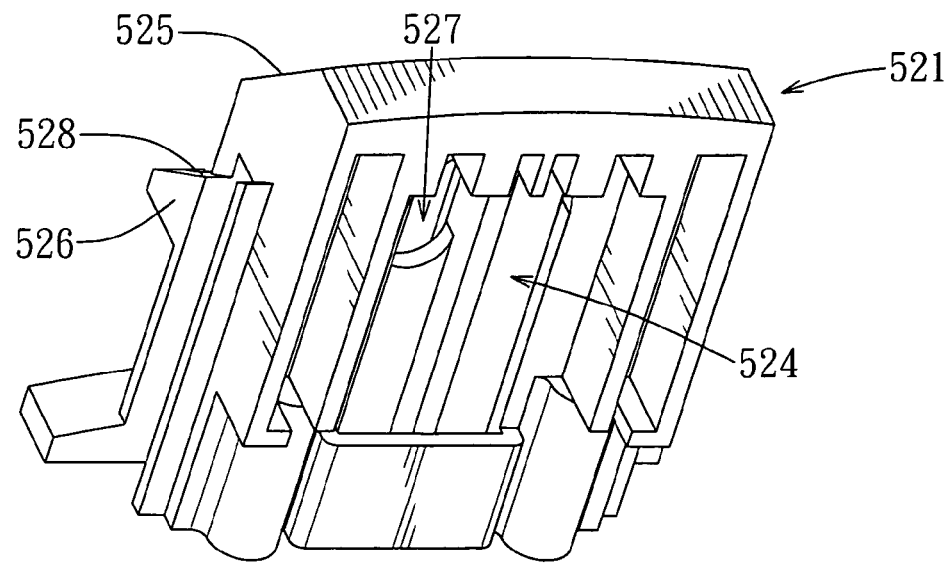
FIG. 10 is a perspective view of a clamping member of the first preferred embodiment.
Figure 11:
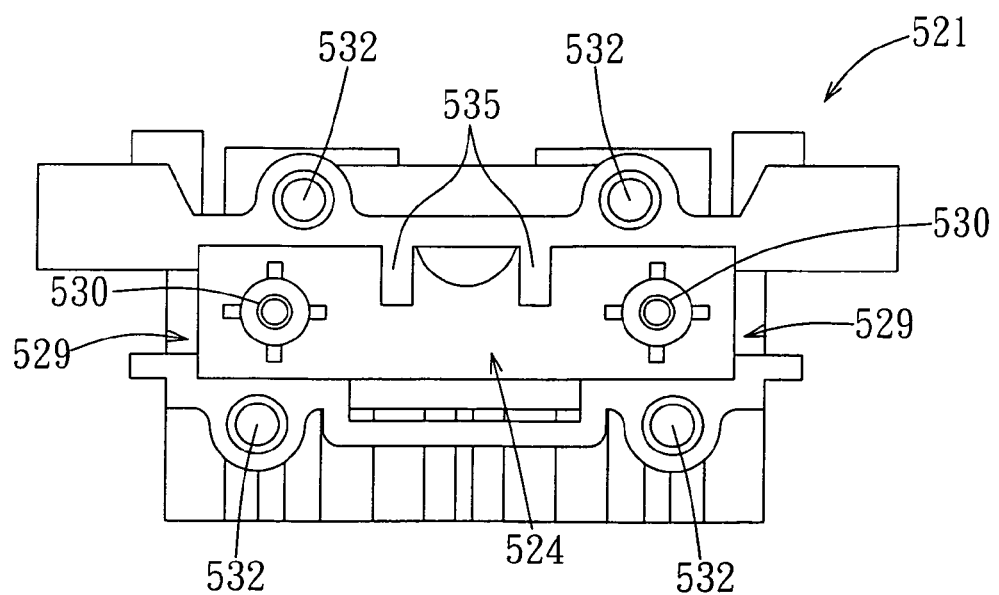
FIG. 11 is a side view of a clamping body of the clamping member of the first preferred embodiment.

With further reference to FIGS. 10 and 11, each of the clamping members 52 includes a clamping body 521 and a cover 522 connected fixedly to the clamping body 521 by a plurality of screws 523 to define a receiving space 524 that is opened downwardly and that permits the corresponding sliding member 51 and the corresponding springs 53 to be disposed therein. Each of the clamping bodies 521 is movable horizontally on the corresponding sliding member 51 along the radial direction of the positioning frame 4, and has a first inclined face 525 that is disposed at a radial outer end thereof adjacent to the pressing ring portion 42 of the positioning frame 4 and that is inclined inwardly and upwardly, two positioning portions 526 disposed respectively at two opposite sides thereof, and an elongated guide hole 527 formed in a top end thereof and in spatial communication with the receiving space 524. The guide holes 527 of the clamping members 52 of each cooperative pair of the clamping mechanisms 5 have closed inner ends 533 adjacent to each other, and closed outer ends 534 opposite respectively to the inner ends 533. Each of the positioning portions 526 has a second inclined face 528 that is inclined upwardly and inwardly. The first inclined faces 525 of the clamping bodies 511 are movable into contact with the inner peripheral surface 22 of the ceiling 2. The second inclined faces 528 are movable into contact with the guiding faces 432, respectively. Each of the clamping bodies 521 further has two open-ended slots 529 permitting the extension arms 513 of the corresponding sliding member 51 to extend respectively therethrough such that the sliding ends 516 of the extension arms 513 of the corresponding sliding member 51 are disposed outwardly of the corresponding clamping body 521 and the threaded hole 517 in the corresponding nut 512 is aligned with the guide hole 527 in the corresponding clamping body 521, and two spring-positioning rods 530 disposed fixedly in the corresponding receiving space 524. Each of the springs 53 is configured as a coiled compression spring, and has one end sleeved on the corresponding spring-positioning rod 530, and the other end abutting against the sliding body 511 of the corresponding sliding member 51. Alternatively, the springs 53 may be in the form of reeds.

Figure 12:
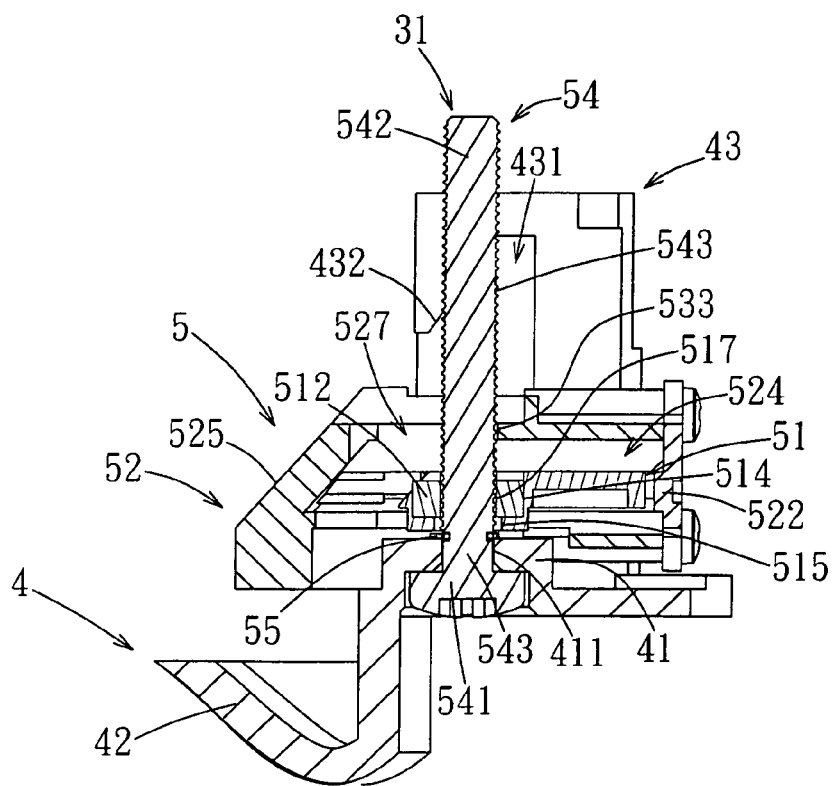
FIG. 12 is a fragmentary sectional view of the first preferred embodiment.

With further reference to FIG. 12, each of the height-adjusting members 54 is configured as an adjustment bolt, and has a head 541, a threaded stem portion 542 disposed above the head 541, and a non-threaded stem portion 543 connected between the head 541 and the threaded stem portion 542. Each of the height-adjusting members 54 extends through the corresponding through hole 411 in the positioning frame 4, the nut-receiving recess 514 and the central hole 515 in the corresponding sliding member 51, and the guide hole 527 in the corresponding clamping member 52, so as to engage the threaded hole 517 in the corresponding nut 512 with the threaded stem portion 542.

Each of the C-shaped retaining rings 55 is sleeved on the non-threaded portion 543 of the corresponding height-adjusting member 54, and abuts against the frame body 41 of the positioning frame 4 so as to prevent vertical movement of the height-adjusting member 54 relative to the positioning frame 4. As such, rotation of each of the height-adjusting members 54 can result in vertical movement of the corresponding sliding member 51 relative to the positioning frame 4 along the corresponding vertical guide slots 431 between a lower limit position shown in FIG. 12 and an upper limit position shown in FIG. 20. For each of the clamping mechanisms 5, the second inclined faces 528 are positioned relative to the inclined guiding faces 432 such that, when the sliding member 51 is disposed in the lower limit position, the clamping member 52 is biased by the springs 53 to an extended position whereat the height-adjusting member 54 is disposed at the inner end 533 of the guide hole 527, and when the sliding member 51 is disposed in the upper limit position, the clamping member 52 is disposed in a retracted position whereat the height-adjusting member 54 is disposed at the outer end 534 of the guide hole 527.

The assembly process of each of the clamping mechanisms 5 includes the following steps:
(1) One end of each of the springs 53 is sleeved on the corresponding spring-positioning rod 530.
(2) The extension arms 513 of the sliding member 51 are inserted into the open-ended slots 529 in the clamping member 52 so that the sliding member 51 is moved into the receiving space 524 in such a manner to allow the other end of each of the springs 53 to abut against the sliding body 511. In this time, the sliding ends 516 of the extension arms 513 are disposed outwardly of the clamping body 521.
(3) The screws 523 are moved respectively through holes 531 in the cover 522 to engage respectively threaded holes 532

(see FIG. 11) in the clamping body 521, thereby forming an assembly of the sliding member 51 and the clamping member 52, in which the nut 512 is confined within the nut-receiving recess 514 in the sliding member 51 by two limiting ribs 535 (see FIG. 11).

(4) The assembly of the sliding member 51 and the clamping member 52 is moved toward the protrusions 43 of the corresponding protrusion unit so that the sliding ends 516 of the extension arms 513 slide into the vertical guide slots 431 in the protrusions 43 via passages 433 in bottom end portions of the protrusions 43 to thereby come into contact with vertical faces 434 defining outer sides of the vertical guide slots 431.

(5) The height-adjusting member 54 is moved through the corresponding through hole 411 in the frame body 41 of the positioning frame 4 and the central hole 515 in the sliding member 51 to engage the threaded hole 517 in the nut 512. Subsequently, the height-adjusting member 54 is further moved through the guide hole 527 in the clamping member 52.

(6) The C-shaped retaining ring 55 is sleeved on the non-threaded stem portion 543 of the height-adjusting member 54 to clamp the frame body 41 of the positioning frame 4 between the head 541 of the height-adjusting member 54 and the C-shaped retaining ring 55, thereby completing the assembly of the clamping mechanism 5.

Operation of one cooperative pair of the clamping mechanisms 5 will be described in the succeeding paragraphs.

Figure 13:
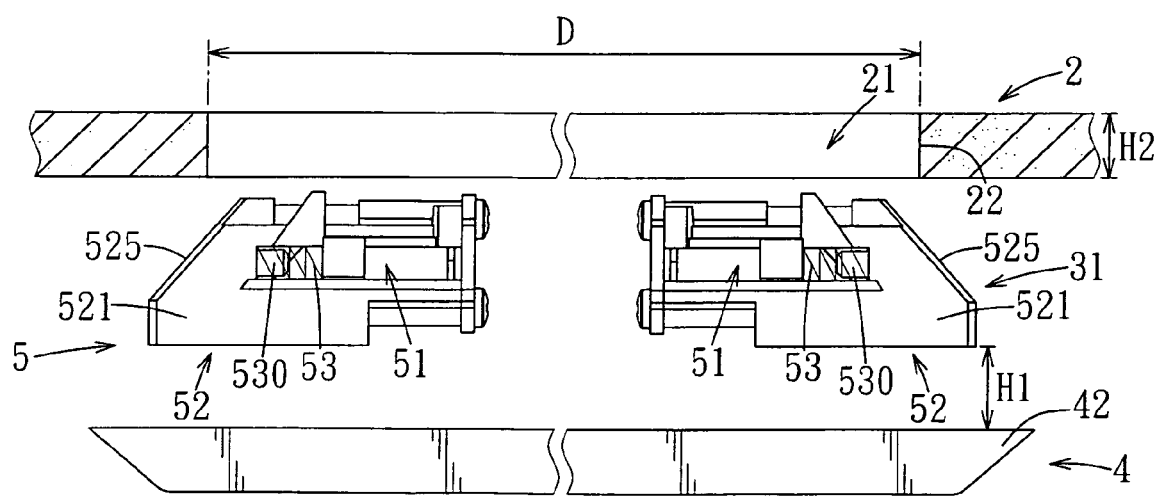
FIGS. 13 to 17 are schematic side views illustrating how the speaker assembly is assembled to the ceiling.
Figure 14:
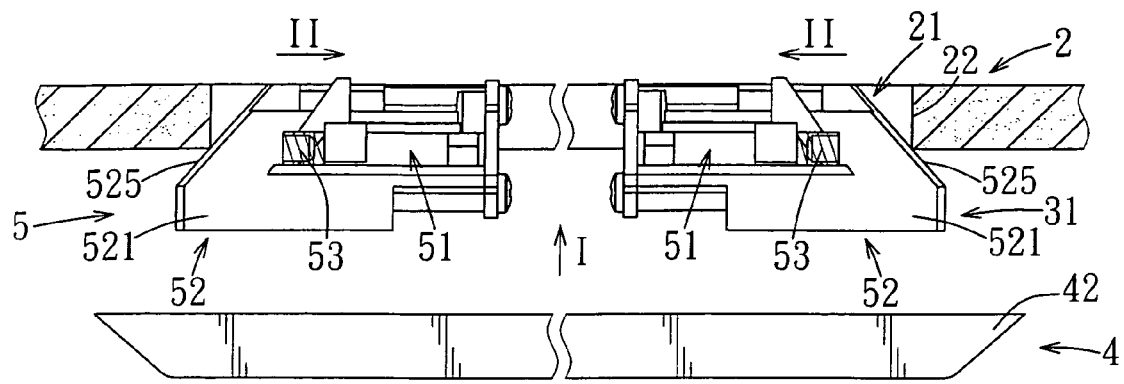

When it is desired to mount the speaker assembly 300 into the mounting hole 21 in the ceiling 2, the height-adjusting members 5 are first operated to move the clamping bodies 521 of the clamping members 52 upwardly relative to the positioning frame 4 to positions shown in FIG. 13 whereat the clamping bodies 521 are spaced apart from the pressing ring portion 42 by a vertical distance (H1) that is slightly smaller than the thickness (H2) of the ceiling 2. Next, with reference to FIG. 14, the clamping mechanisms 5 are moved into the mounting hole 21 in the ceiling 2 in an upward direction (I) such that the first inclined faces 525 slide on a bottom end of the inner peripheral surface 22 of the ceiling 2, thereby allowing the clamping members 52 to be pushed and moved by the inner peripheral surface 22 toward each other in inward directions (II).

Figure 15:
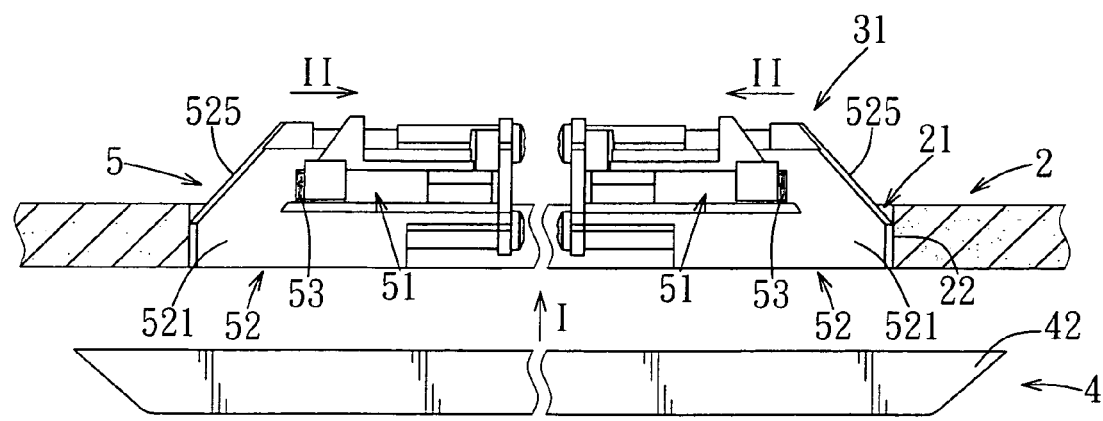

With reference to FIG. 15, when each of the clamping members 52 is moved to the retracted position due to the pushing of the inner peripheral surface 22, the distance between the outer ends of the clamping members 52 is smaller than the diameter (D) of the mounting hole 21. Hence, the outer ends of the clamping members 52 slide upwardly on the inner peripheral surface 22 until they pass through the mounting hole 21.

Figure 16:
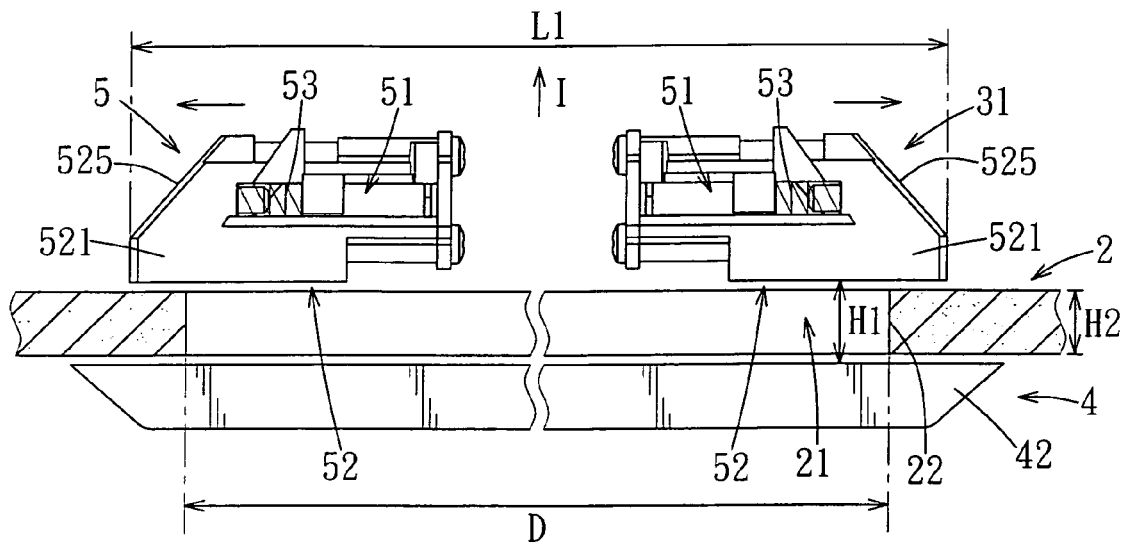

Referring to FIG. 16, the clamping members 52 are biased by the springs 53 to move away from each other to the extended positions immediately after they pass through the mounting hole 21. In the extended positions, the distance (L1) between the outer ends of the clamping members 52 is greater than the diameter (D) of the mounting hole 21.

Figure 17:
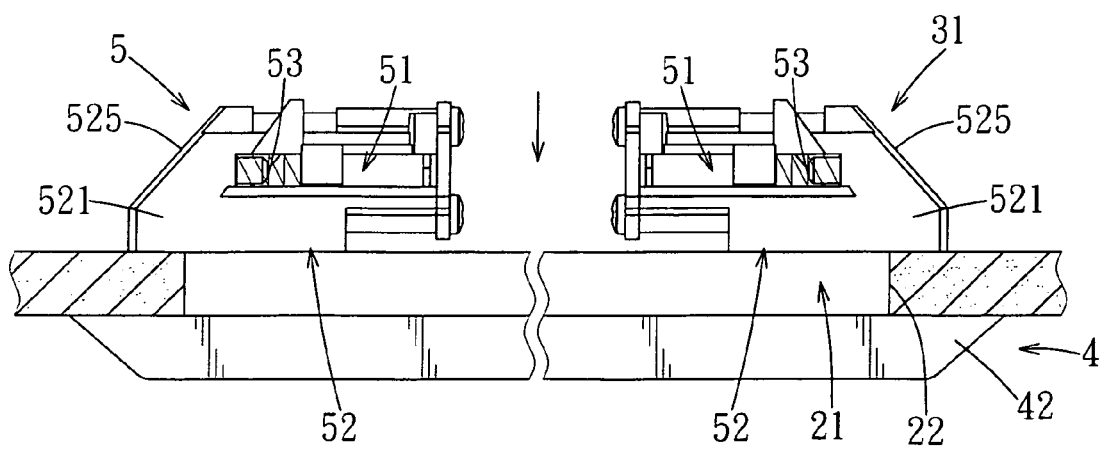

Subsequently, with reference to FIG. 17, the height-adjusting members 54 (see FIG. 12) are operated to move the clamping members 52 downwardly relative to the positioning frame 4 so as to clamp the ceiling 2 between the pressing ring portion 42 and the clamping bodies 521 of the clamping members 52, thereby mounting the speaker assembly 300 fixedly to the ceiling 2.

During assembly, the clamping members 52 are biased to the extended positions immediately after they are moved upwardly through the mounting hole 21 in the ceiling 2. At this time, since the distance between outer ends of the clamping members 52 is greater than the diameter (D) (see FIG. 16) of the mounting hole 21, the clamping members 52 are supported by the ceiling 2 so that the height-adjusting member 54 can be operated easily to clamp the ceiling 2 between the positioning frame 4 and the clamping members 52. Thus, the object of this invention is achieved.

Figure 18:
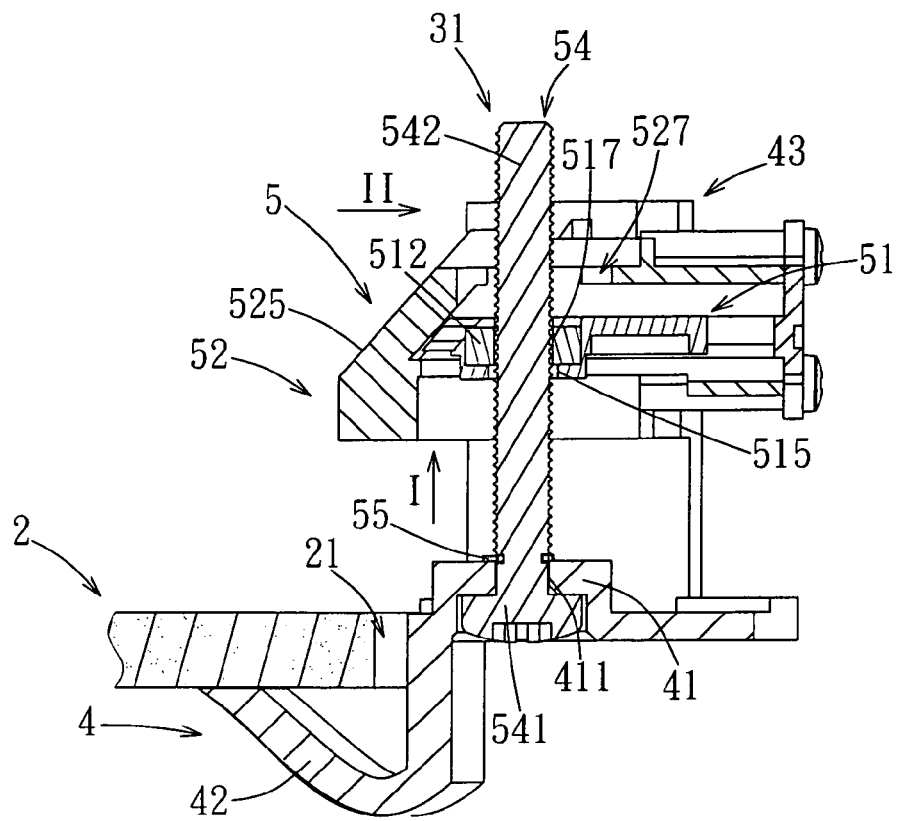
FIGS. 18 to 21 are schematic views illustrating how the speaker assembly is disassembled from the ceiling.
Figure 19:
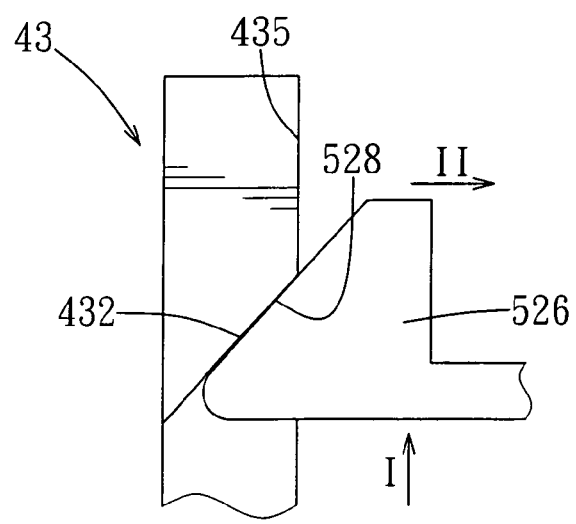

With reference to FIG. 18, when it is desired to remove the speaker assembly 300 from the ceiling 2, the height-adjusting member 54 is operated to move the clamping members 52 upwardly relative to the positioning frame 4. During upward movement of the clamping members 52, the second inclined faces 528 come into contact with the inclined guiding faces 432 of the protrusions 43, respectively. With reference to FIG. 19, when each of the second inclined faces 528 slides on the corresponding inclined guiding face 432 in the upward direction (I), the corresponding clamping member 52 is pushed by the corresponding inclined guiding face 432 toward the retracted position in the inward direction (II).

Figure 20:
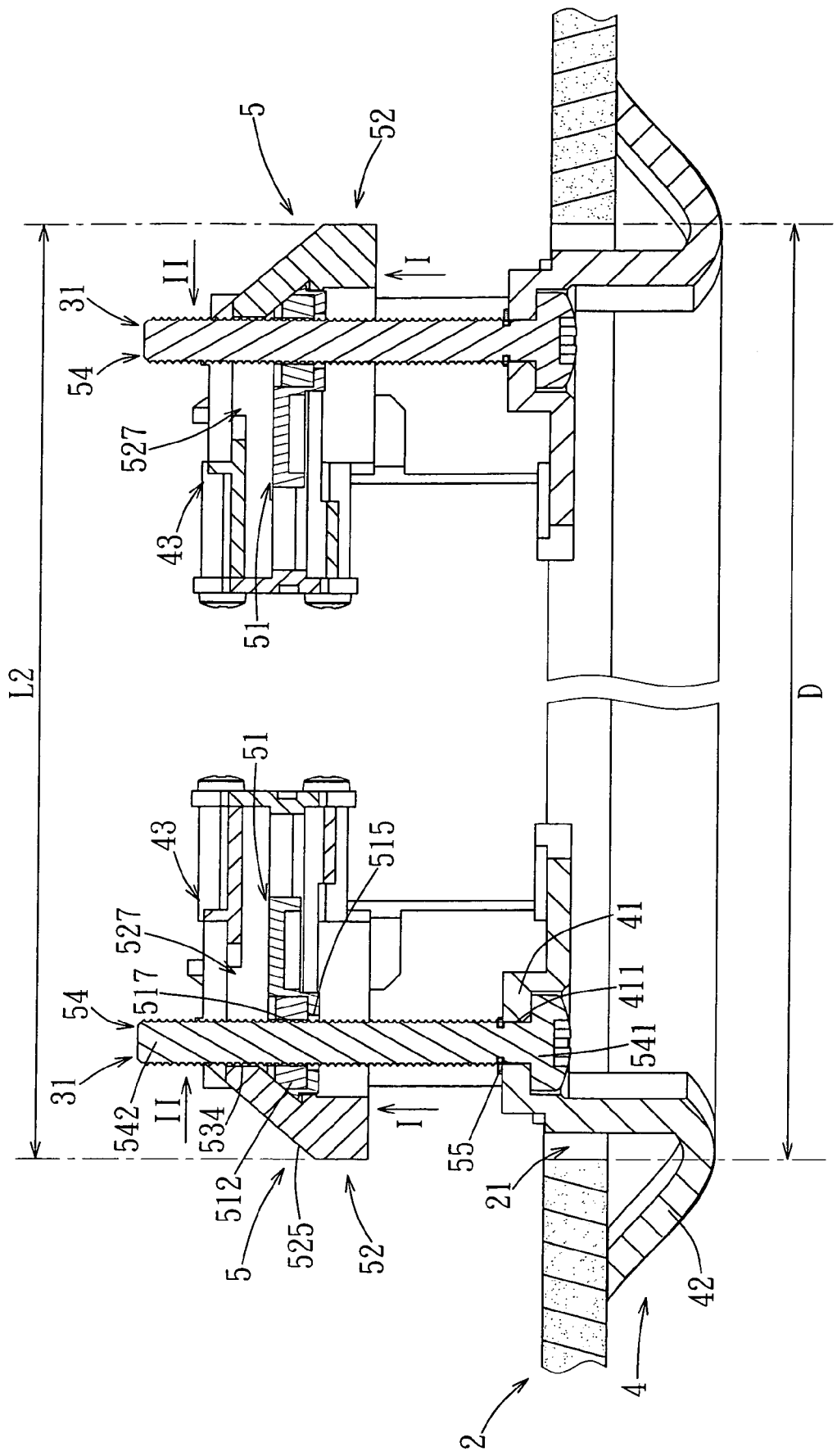
Figure 21:
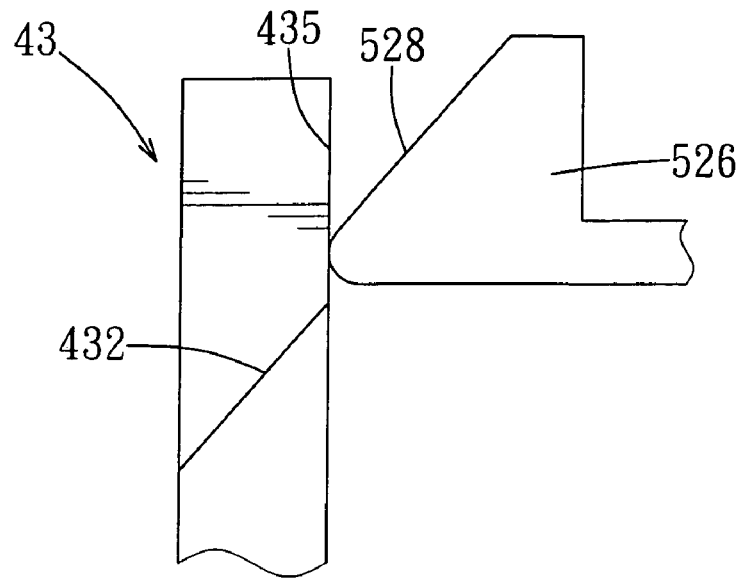

Referring to FIG. 20, when the sliding members 51 reach the upper limit positions, the distance (L2) between the outer ends of the clamping members 52 is smaller than the diameter (D) of the mounting hole 21. At this time, with further reference to FIG. 21, the clamping members 52 are disposed in the retracted positions, and the positioning portions 526 abut respectively against two vertical stop faces 435, which have lower ends connected respectively to upper ends of the inclined guiding faces 432, so as to maintain the clamping members 52 in the retracted positions. Hence, the clamping mechanisms 5 can be moved downwardly through the mounting hole 21.

Figure 22:
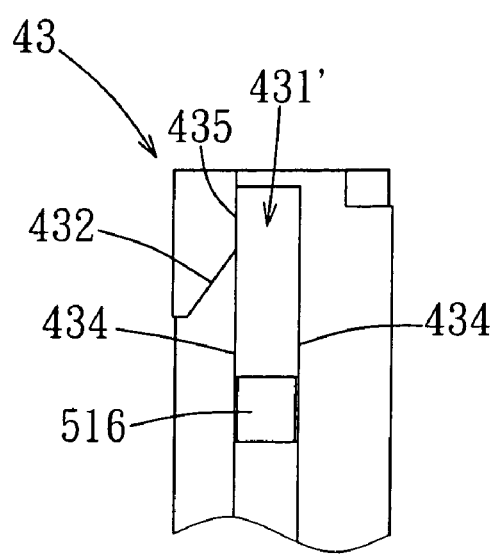
FIG. 22 is a fragmentary schematic side view of a protrusion of a positioning frame of the second preferred embodiment of a speaker assembly according to this invention.

The second preferred embodiment of a speaker assembly according to this invention is similar in construction to the first preferred embodiment except that each protrusion unit includes only one protrusion 43. With reference to FIG. 22, in this embodiment, the passage 433 is omitted from the protrusion 43, and the vertical guide slot 431' is defined by two vertical faces 434 having bottom ends disposed at a bottom end of the protrusion 43.

With this invention thus explained, it is apparent that numerous modifications and variations can be made without departing from the scope and spirit of this invention. It is therefore intended that this invention be limited only as indicated by the appended claims.

I claim:

1. A mounting device adapted to mount an electronic device to a horizontal plate, the plate having a mounting hole formed therethrough and defined by an inner peripheral surface, said mounting device comprising:

a positioning frame including a frame body adapted to be mounted with the electronic device, a pressing ring portion disposed around said frame body, and at least two vertical through holes formed through said frame body; and at least one cooperative pair of clamping mechanisms disposed on said positioning frame, each of said clamping mechanisms including a sliding member movable vertically relative to said positioning frame, a clamping member disposed movably on said sliding member and having a first inclined face that is adjacent to said pressing ring portion of said positioning frame and that is inclined inwardly and upwardly, said clamping member being movable on said sliding member between an extended position whereat an assembly of said sliding member and said clamping member is sized so as not to move through the mounting hole in the plate, and a retracted position whereat the assembly of said sliding member and said clamping member is movable through the mounting hole in the plate, a spring disposed between said sliding member and said clamping member for biasing said clamping member toward said extended position, and a height-adjusting member extending through a corresponding one of said through holes in said positioning frame and operable to move said sliding member and said clamping member vertically relative to said positioning frame;

wherein, when said clamping members of said clamping mechanisms are moved upwardly into the mounting hole in the plate, said first inclined faces of said clamping members slide on a bottom end of the inner peripheral surface of the plate so that each of said clamping members is moved to said retracted position, thereby allowing said clamping members to move through the mounting hole in the plate; and subsequently, said height-adjusting members can be operated to move downwardly said sliding members and said clamping members of said clamping mechanisms relative to said positioning frame so as to clamp the plate between said pressing ring portion of said positioning frame and said clamping members.

2. The mounting device as claimed in claim 1, wherein said clamping mechanisms are disposed respectively at two diametrically opposite locations relative to said positioning frame, said clamping members having outer ends spaced apart from each other by a distance that is greater than the diameter of the mounting hole when each of said clamping members is disposed in said extended position, and smaller than the diameter of the mounting hole when each of said clamping members is disposed in said retracted position.

3. The mounting device as claimed in claim 1, wherein:
said positioning frame further includes at least two protrusion units adjacent respectively to said through holes, each of said protrusion units extending upwardly from said frame body and having at least one guiding face that is inclined upwardly and inwardly;
each of said sliding members is movable relative to said positioning frame between an upper limit position and a lower limit position; and
each of said clamping members further includes a second inclined face that is inclined upwardly and inwardly and that is movable into contact with said guiding face of a corresponding one of said protrusion units of said positioning frame so that, a corresponding one of said clamping members is disposed in said extended position when a corresponding one of said sliding members is disposed in said lower limit position, and the corresponding one of said clamping members is disposed in said retracted position when the corresponding one of said sliding members is disposed in said upper limit position.

4. The mounting device as claimed in claim 3, wherein:
each of said clamping members further includes a positioning portion that has said second inclined face; and
each of said protrusion units of said positioning frame further has a vertical stop face connected to an upper end of said guiding face at a lower end thereof and positioned so that said positioning portion of a corresponding one of said clamping members comes into contact with said stop face when the corresponding one of said clamping members is moved to said retracted position, thereby maintaining the corresponding one of said clamping members in said retracted position.

5. The mounting device as claimed in claim 3, wherein:
each of said protrusion units of said positioning frame includes two aligned protrusions formed respectively with two parallel vertical guide slots; and
each of said sliding members includes a sliding body and two extension arms extending respectively from two opposite sides of said sliding body and movable respectively within said guide slots in said protrusions of a corresponding one of said protrusion units.

6. The mounting device as claimed in claim 1, wherein:
each of said sliding members is formed with a threaded hole;
each of said height-adjusting members is configured as a vertical adjustment bolt, and has a head abutting against said frame body of said positioning frame, a threaded stem portion disposed above said head and engaging said threaded hole in a corresponding one of said sliding members, and a non-threaded stem portion connected between said head and said threaded stem portion; and
each of said clamping mechanisms further includes a C-shaped retaining ring sleeved on said non-threaded portion of said adjustment bolt and abutting against said frame body of said positioning frame so as to prevent vertical movement of said adjustment bolt relative to said positioning frame.

7. The mounting device as claimed in claim 1, wherein each of said clamping members is formed with a receiving space that is opened downwardly and that permits a corresponding one of said sliding members to be disposed therein, two open-ended slots permitting said extension arms of the corresponding one of said sliding members to extend respectively therethrough, and an elongated guide hole formed in a top end of the corresponding one of said clamping members and permitting a corresponding one of said height-adjusting members to extend therethrough.

8. The mounting device as claimed in claim 7, wherein said guide holes in said clamping members have closed inner ends adjacent to each other and permitting said height-adjusting members of said clamping mechanism to be disposed thereat when each of said clamping members is disposed in said extended position, and closed outer ends opposite respectively to said inner ends and permitting said height-adjusting members to be disposed respectively thereat when each of said clamping members is disposed in said retracted position.

9. The speaker assembly as claimed in claim 1, wherein said clamping mechanisms are adapted to be disposed respectively at two diametrically opposite locations relative to said positioning frame, said clamping members having outer ends that are spaced apart from each other by a distance that is greater than the diameter of the mounting hole when each of said clamping members is disposed in said extended position, and smaller than the diameter of the mounting hole when each of said clamping members is disposed in said retracted position.

10. The speaker assembly as claimed in claim 1, wherein:
said positioning frame further includes at least two protrusion units adjacent respectively to said through holes, each of said protrusion units extending upwardly from said frame body and having at least one guiding face that is inclined upwardly and inwardly;
each of said sliding members is movable relative to said positioning frame between an upper limit position and a lower limit position; and
each of said clamping members further includes a second inclined face that is upwardly and inwardly and that is movable into contact with said guiding face of a corresponding one of said protrusion units of said positioning frame so that, a corresponding one of said clamping members is disposed in said extended position when a corresponding one of said sliding members is disposed in said lower limit position, and the corresponding one of said clamping members is disposed in said retracted position when the corresponding one of said sliding members is disposed in said upper limit position.

11. The speaker assembly as claimed in claim 3, wherein:
each of said clamping members further includes a positioning portion that has said second inclined face; and
each of said protrusion units of said positioning frame further has a vertical stop face connected to an upper end of said guiding face at a lower end thereof and positioned so that said positioning portion of a corresponding one of said clamping members comes into contact with said stop face when the corresponding one of said clamping members is moved to said retracted position, thereby maintaining the corresponding one of said clamping members in said retracted position.

12. The speaker assembly as claimed in claim 3, wherein:
each of said protrusion units of said positioning frame includes two aligned protrusions formed respectively with two parallel vertical guide slots; and
each of said sliding members includes a sliding body and two extension arms extending respectively from two opposite sides of said sliding body and movable respectively within said guide slots in said protrusions of a corresponding one of said protrusion units.

13. The speaker assembly as claimed in claim 1, wherein:
each of said sliding members is formed with a threaded hole;
each of said height-adjusting members is configured as a vertical adjustment bolt, and has a head abutting against said frame body of said positioning frame, a threaded stem portion disposed above said head and engaging said threaded hole in a corresponding one of said sliding members, and a non-threaded stem portion connected between said head and said threaded stem portion; and
each of said clamping mechanisms further includes a C-shaped retaining ring sleeved on said non-threaded portion of said adjustment bolt and abutting against said frame body of said positioning frame so as to prevent vertical movement of said adjustment bolt relative to said positioning frame.

14. The speaker assembly as claimed in claim 1, wherein each of said clamping members is formed with a receiving space that is opened downwardly and that permits a corresponding one of said sliding members to be disposed therein, two open-ended slots permitting said extension arms of the corresponding one of said sliding members to extend respectively therethrough, and an elongated guide hole formed in a top end of the corresponding one of said clamping members and permitting a corresponding one of said height-adjusting members to extend therethrough.

15. The speaker assembly as claimed in claim 7, wherein said guide holes in said clamping members have closed inner ends adjacent to each other and permitting said height-adjusting members of said clamping mechanism to be disposed thereat when each of said clamping members is disposed in said extended position, and closed outer ends opposite respectively to said inner ends and permitting said height-adjusting members to be disposed respectively thereat when each of said clamping members is disposed in said retracted position.

16. A speaker assembly adapted to be mounted to a horizontal plate, the plate having a mounting hole that is formed therethrough and that is defined by an inner peripheral surface, said speaker assembly comprising:
a speaker; and
a mounting device including
a positioning frame including a frame body adapted to be mounted with the speaker, a pressing ring portion disposed around said frame body, and at least two vertical through holes formed through said frame body, and
at least one cooperative pair of clamping mechanisms disposed on said positioning frame, each of said clamping mechanisms including
a sliding member movable vertically relative to said positioning frame,
a clamping member disposed movably on said sliding member and having a first inclined face that is adjacent to said positioning ring portion of said positioning frame and that is inclined inwardly and upwardly, said clamping member being movable on said sliding member between an extended position whereat an assembly of said sliding member and said clamping member is sized so as not to move through the mounting hole in the plate, and a retracted position whereat the assembly of said sliding member and said clamping member is movable through the mounting hole in the plate,
a spring disposed between said sliding member and said clamping member for biasing said clamping member toward said extended position, and
a height-adjusting member extending through a corresponding one of said through holes in said positioning frame and operable to move said sliding member and said clamping member vertically relative to said positioning frame;
wherein, when said clamping members of said clamping mechanisms are moved upwardly into the mounting hole in the plate, said first inclined faces of said clamping members slide on a bottom end of the inner peripheral surface of the plate so that each of said clamping members is moved to said retracted position, thereby allowing said clamping members to move through the mounting hole in the plate; and subsequently, said height-adjusting members can be operated to move downwardly said sliding members and said clamping members of said clamping mechanisms relative to said positioning frame so as to clamp the plate between said pressing ring portion of said positioning frame and said clamping members.

\* \* \* \* \*